(12) United States Patent
Dobler et al.

(10) Patent No.: US 8,541,358 B2
(45) Date of Patent: Sep. 24, 2013

(54) FRAGRANT GEL POLYMER WITH WATER

(75) Inventors: Sven Dobler, Huntington, NY (US); Long Tran, Ronkokoma, NY (US)

(73) Assignee: Orlandi, Inc, Farmingdale, NY (US)

( * ) Notice: Subject to any disclaimer, the term of this patent is extended or adjusted under 35 U.S.C. 154(b) by 0 days.

(21) Appl. No.: 13/135,373

(22) Filed: Jul. 1, 2011

(65) Prior Publication Data
US 2012/0322716 A1 Dec. 20, 2012

Related U.S. Application Data

(60) Provisional application No. 61/399,225, filed on Jul. 8, 2010.

(51) Int. Cl.
*A61L 9/04* (2006.01)
(52) U.S. Cl.
USPC .............................................................. 512/4
(58) Field of Classification Search
USPC .............................................................. 512/4
See application file for complete search history.

(56) References Cited

U.S. PATENT DOCUMENTS

2009/0149566 A1* 6/2009 Dobler .......................... 523/102
2010/0160453 A1* 6/2010 Koivisto et al. ............... 514/724

* cited by examiner

*Primary Examiner* — Ling Choi
*Assistant Examiner* — Lanee Reuther
(74) *Attorney, Agent, or Firm* — Paul M. Denk

(57) ABSTRACT

The fragrant gel polymer system is a process where a fragrance formulation is divided and blended with a polymer and a cross-linking agent. The polymer is then liquefied and made homogenous with a solvent, including esters. The solvent modifies viscosity and later eases the mixing of the polymer with the cross-linking agent. The cross linking agent is then liquefied and blended with water and aliphatic alcohol reducing steric hindrance. Mixing of the fragrance carrying polymer and the cross linking agent results in a gel that sets in less time and with less syneresis than existing processes. The resulting gel achieves a near transparent form and receives dyes while attaining various molded shapes.

2 Claims, 2 Drawing Sheets

US 8,541,358 B2

FRAGRANT GEL POLYMER WITH WATER

CROSS REFERENCE TO RELATED APPLICATION

This non provisional patent application claims priority to the provisional patent application having Ser. No. 61/399,225, having a filing date of Jul. 8, 2010.

BACKGROUND OF THE INVENTION

This fragrant gel polymer system with water relates to the manufacture of fragrant gels and more specifically to a process of mixing two fragrance components with water and alcohol. A unique aspect of the system is a reduction in syneresis, the control and reduction of steric hindrance of the components resulting in a more producible and consistent process during manufacturing and a more stable product overall. It can also lead to a more transparent gel than when using ionic surfactants.

A variety of gel products are on the market, used mostly for toys, novelties, gifts, window clings, and decorative ornaments. Consumers are particularly attracted by the gel products due to their features of softness, color, and introduction of a scent or fragrance. These features, desired by consumers, are related to the nature of the gel product, containing fragrance material. These fragrance materials remain liquid at room temperatures and may separate from the gel product when the gel product contracts slightly during syneresis. Additionally, the careful selection of the composition of gel products and fragrance materials can improve the release of a scent, or fragrance, from the surface of the gel products for introduction into the atmosphere.

A fragrant gel product results from the cross-linking between a functionalized polymer and a cross-linking agent both generally liquid in the presence of a single or a multiple part fragrance base. The polymer crosslinks in the presence of the fragrance to form a gel which encloses the perfume, or fragrance. The gel can form in a recess in a substrate as an air freshener device, as a block, and the like.

While mixing the fragrance, polymer, and cross-linking agent, forms a practical homogeneous mixture, such a mixture poorly controls the flow of the cross-linking agent in a small volume. For a better gel product, equalizing the flow rates of the different premixes into the final mixing step has had more positive results. Accordingly, the fragrance acquires a formulation by conventional methods and then a portion of the fragrance mixes with the polymer and the remainder of the fragrance mixes with the cross-linking agent. The two mixtures can then be mixed together to form a mixture that gels. As the fragrance remains separated within the two mixtures, the mixture containing the cross-linking agent has a greater volume than the volume of the cross-linking agent alone, and therefore a greater flow rate, more easily controlled.

Though this mixture method works well when the production line starts, the gel produced by the mixture method worsens after the production line has run for a time. The gelling time of the mixture, i.e. the time required for a non-flowing gel to form into a shape, tends to rise over time. This longer forming time causes problems into the manufacturing shift, especially at the end of a shift, on an operating machine. For example, if the gelling time of the mixture increases and exceeds the time that the containers, containing the fragrance elements, occupy the production line, the gel may have partially solidified and may retain some liquid when the containers, or forms, are removed from the production line. This liquid can spill from the forms, or containers, leading to waste of ingredients, disruption of the production line for cleaning, and release of spilled ingredients into the local sewerage system. In addition, the actual gel matrix formation is impaired after long pre-bleed times resulting in products that are less stable and more prone to breakdown and liquefaction. This is due to the fragrance materials pre-reacting and consuming reactive gel matrix sites, or polymers and cross linkers.

Fragrances usually contain components which react with either, or both, of the functionalized polymer and the cross-linking agent. The prior art processes have the functionalized polymer and cross-linking agent each mixing with different parts of the fragrance, before the polymer and the cross-linking agent are mixed. Thus the functionalized polymer and cross-linking agents mix with separate fragrance components, not the same fragrance composition. Instead, the gel product has a final fragrance composition arranged, and different components of the composition are then mixed with the functionalized polymer and with the cross-linking agent. By separating the fragrance components, the issue of incomplete gel matrix formation decreases to a practical extent or even completely ceases. The problem with this is that it is costly to develop two separate fragrance modifications that need to be brought back to exactly the right ratio to result in the intended and desired olfactive result. The problem also includes no manufacturing flexibility. Further, slight changes in mix rates can affect fragrance olfactive/character shift.

While the precise ingredients of any particular fragrance often remain trade secrets kept by the fragrance oil purveyor and remain unknown to the manufacturer of a fragrant product, the typical classes of ingredients, and particularly common ingredients, include volatile compounds such as esters, alcohols, aldehydes and ketones. As before, the functionalized polymers and cross-linking agents react with certain fragrance ingredients but not others, not entirely known by the product manufacturer. The reaction rate may be relatively slow and that does not appear early in a manufacturing shift but, after the fragrance ingredients have been mixed with the functionalized polymer and cross-linking agent for some time, a few hours in many cases, some of the fragrance components will have reacted as a pre-reaction. Alas, these pre-reactions may undesirably affect the fragrance, varying its fragrance over a production run. Furthermore, the pre-reactions consume some of the functionalized polymer and cross-linking agent, thus reducing the concentration of reactive sites of the functionalized polymer and the cross-linking agent later in the production run. The pre-reactions have an often increased setting time using prior art methods and processes. Once again, the actual gel matrix formation is impaired after long pre-bleed times resulting in products that are less stable and more prone to breakdown and liquefaction. This is due to the fragrance materials pre-reacting and consuming reactive gel matrix sites, or polymers and cross linkers.

The functional polymer has one or more functional groups while the cross-linking agent has one or more complimentary functional groups. The mixture of these two provides, in the presence of a fragrance base, a reaction product that encloses or entraps the fragrance base in a gel product which then emanates the fragrance to the atmosphere to freshen the air. Suitable functional groups include carboxylic acid, anhydride or acid chloride groups, amines, and alcohols. The functional polymer forms by adding a functional group to any polymer capable of functionalization, or the polymer itself inherently contains functional groups. The functional groups can be pendent on the main chain perhaps with intervening spacer groups or in the main chain. Preferred polymers for functionalization include polyolefins, particularly those derived from mono-olefins or di-olefins containing, at least one vinyl group.

The cross-linking agent generally dissolves in the fragrance base. Suitable cross-linking agents include dihydroxy polybutadiene, alkoxylated primary amines, alkylpropyldiamines having an ethoxylated or propoxylated fatty aliphatic chain, diethanolamine, diethylenetriamine, polyoxyalkylenediamines and alkoxylated primary fatty amines. The cross-linking agent may have one or more diamines or triamines, polyoxyalkylene amines, polyethoxy diamines and triamines, polypropoxy diamines and triamines.

Within the prior art, the fragrance is a mixture of volatile liquid ingredients of natural or synthetic origin. Lists and descriptions of the ingredients for a fragrance appear in perfumery books, for example in S. Arctander, *Perfume and Flavour Chemicals*, Montclair, N.J., USA, 1969 and the like. The art of formulating a fragrance begins with devising a base and at least a note having the desired fragrance, a common task carried out by a fragrance manufacturer.

Generally, the cross-linking agent reacts with some of the fragrance components, while the functionalized polymer does not appreciably react during a typical production shift. The prior art separates the components of a fragrance into those components of the fragrance which react, or are likely to react, with the cross-linking agent and those components which do not react, or are unlikely to react. Individual fragrance components which do not react with either the functionalized polymer or the cross-linking agent may be mixed with either polymer or cross-linking agent at the discretion of the fragrance manufacturer.

DESCRIPTION OF THE PRIOR ART

Two main gel process patents guide the formulation and manufacture of gels. The first is U.S. Pat. No. 6,846,491 to Richards, which describes a clear polymeric gel of cross-linked polymers. For instance, the polymers include Lithene®, from Struktol Co. of America, Stow, Ohio, distributor for Synthomer® of the United Kingdom for Phase 1 and Jeffamine®, by Huntsman® Corp. of Salt Lake City, Utah for Phase 2. The fragrance begins as fragrant oil formulations of both organic and inorganic aroma chemicals along with other ingredients used to prepare fragrances. The fragrant oil formulations are blended with both Lithene® and Jeffamine® generally and with an ionic surfactant such as Steol® by Stepan® Co. of Chicago, Ill. The fragrance oils pre-mix readily in Phases 1 and 2 thus making each phase homogeneous and fostering ready combination and mixture of Phases 1 and 2. The Richards method entraps the active aroma chemicals and produces a solid gel in less than 45 minutes. The Richards method also avoids the heat dependent formulations or those created at room temperature as known in the art. The heat dependent formulations run the risk of altering, modifying, or destroying the fragrance oils when the volatile organic compounds within the fragrance oils evaporate or break down.

Additionally, the gel polymer system and process by Richards have high reactivity and react early with colorants and pigments during gel manufacturing. The polymers exhibit problems with color fastness. The polymers also react with aromatic chemicals in fragrance oil formulations thus depleting the cross linker reaction sites before final mixing with other components. The depleted reaction sites lead to imperfect cross linking of Lithene® and Jeffamine® polymers where the fragrance oils later precipitate from the gel, as in syneresis, or the gel becomes unstable, liquefies, and fails.

Formulating fragrances for the Richards method has challenged manufacturers who have faced limits upon usage of fragrance components when creating various cosmetic products. In a few case, manufacturers have been thwarted in combining certain fragrances with gels.

The second gel process patent, U.S. Pat. No. 7,132,461 to O'Leary et al., applies a method of manufacturing fragrance oils making a fragrant gel in two parts. The O'Leary method splits the fragrance oils into two parts, the polymer reactive and the crosslinking agent reactive, such as Lithene® and Jeffamine® respectively. In splitting the oils, each element of a fragrance formulation requires testing for reactivity to various polymers for segregation into polymer and crosslinking agent reactive components. Generally, the polymer reactive parts are blended with crosslinking agent as Phase 1 while the crosslinking agent reactive parts are blended with polymer as phase 2. To form the complete fragrance, the two phases are blended and provide more effective cross linking of polymers because the reactive sites of each polymer have not already reacted with the fragrance components known to favor that polymer. In blending the two phases, the fragrance components assemble and make the whole fragrance as desired by the consumer. The O'Leary method reduces syneresis and shrinkage of the gel product while improving the stability of the finished gel product. However, this method has problems with the cost of formulation, variable outcome, normal process variations in mixing leading to unintended olfactive shift, and fluctuations in ratios of materials.

Various fragrance formulations contain both aldehydes and ketones which can affect the polyetheramine cross linker by forming imines through an addition and elimination process. At the same time, the process forms a minute amount of water. When the process reaches equilibrium, the process has reduced the effectiveness of the polyetheramine to cross link with a polymer. An increase in curing time for a gel indicates the reduced effectiveness of the cross linker. As the cure time increases, the gel matrix forms with less and less structure eventually not forming at all. The reduction in cross linker effectiveness from the aldehydes and ketones becomes a steric hindrance.

By adding water, as later shown in the present invention, this equilibrium can be pushed so as to reduce pre-reaction between ketones and aldehydes with the crosslinker leaving reactive sites available for polymer reaction. Water performs a balancing act as it shifts the affinity of reactions and maintains the intended reactions leading to the desired gel of the present invention. The water assures any pre-reaction with the fragrance remains dormant.

Each atom in a molecule of a chemical occupies a defined space with a outer boundary set by the electron cloud. When atoms approach each other in a molecule, the electron clouds overlap and lessen the energy of the adjacent atoms in a molecule. This lessening of energy is a steric effect and it affects the shape and reactivity of a molecule in various reactions. More particularly, steric hindrance takes place when the size of groups within a molecule prevents chemical reactions that generally occur in smaller molecules related to the larger molecule. Steric hindrance affects the rates and energy of chemical reactions.

However, addition of water or alcohol reverses the process and suppresses the retarding effect, that is, steric hindrance, of the aldehydes and the ketones reacting with the amine cross linkers. Further, the water prevents interference of the aldehydes with the secret or unknown parts of fragrance oil. Water also prevents fragrance molecules from leaving the reaction site on aldehydes thus maintaining a reactive balance. Alcohols include two types, long chain and short chain. Long chain alcohols, including those that may act as surfactants, are known to cloud gels while short chain alcohols are not considered surfactants, do not encapsulate the water, and result therefore in less cloudiness in the gel. The short chain alcohols include ethanol, methanol, and isopropyl alcohol. Prior art attempts to add surfactant show no effect on steric hindrance and further, the surfactants encapsulate each water molecule which prevents it from suppressing the steric hindrance of aldehydes and ketones on the crosslinker. Both the '491 patent to Richards and the patent Pub. No. 2008/0015295 to Williams omit discussion of steric hindrance and the problems it causes in practice and manufacturing.

The present invention overcomes the limitations of the prior art. That is, in the art of the present invention, a fragrant gel polymer system, combines a fragrance formulation, a cross linking agent, a polymer, water, and a short chain alcohol in a certain sequence to suppress the effects of steric hindrance. The present invention blends the fragrance formulation with a polymer. A cross linking agent, having a lesser amount of fragrance, is then mixed with water and alcohol. Both the polymer component and the cross linking component may also include a solvent, such as a member of the ester class. Then the dissolved cross linking agent and dissolved polymer are blended to form a gel of desired fragrance, consistency, or transparency. The gel entraps the fragrance molecules thus reducing evaporative losses over time. Use of aliphatic alcohol and water worked well with the polymer and cross linker and protected the nascent gel matrix from the scavenging effects of aldehydes and ketones on the polyetheramine molecules. The present invention leads to a gel formation being more efficient, consistent, and faster than in the prior art that omitted water and alcohol. The gel resulting from the process of the present invention has more clarity, greater transparency, a more solid matrix, and more aesthetic pleasure than prior art hydrous systems that use surfactants, and it is more consistent in manufacturing and more stable as a finished product.

SUMMARY OF THE INVENTION

The preferred embodiment of the fragrant gel polymer system with water is a method where a fragrance formulation has a major portion and a minor portion, the major portion is then blended with preferably a polymer, such as Lithene® and the minor portion is then blended with a cross linking agent, such as Jeffamine®, water, and an alcohol preferably ethanol. The dissolved polymer and the dissolved cross-linking agent are then blended to produce a nearly transparent gel. The method of the present invention reduces the premature reaction of fragrance materials and the cross linking agent by controlling the effects of steric hindrance. The polymer component, or alternatively the cross linking agent, may be made more homogenous with a solvent, often an ester. The solvents can help modify viscosity and ease the mixing of the polymer and the cross linking agent. Alternatively, the method provides accelerators, but excluding triethanolamine "TEA," for further integration and mixing of the fragrance oils with either the polymer, such as Lithene® or the crosslinking agent such as Jeffamine®. However, the invention is not limited to Lithene® and Jeffamine® usage.

Upon testing, the gel from the process of the invention holds its integrity well and is less prone to liquefaction and breakdown more slowly than the prior art gels. The testing of the present invention simulated real world environmental conditions by a crash test at high temperature. The temperature accelerated chemical breakdown reactions that occur in the environment but at a much slower rate. The gel from the process of the invention withstood the high temperatures better and thus leads to a conclusion that the present invention yields gels to be more robust and stable over longer time intervals.

Numerous objects, features and advantages of the present invention will be readily apparent to those of ordinary skill in the art upon a reading of the following detailed description of the presently preferred, but nonetheless illustrative, embodiment of the present invention when taken in conjunction with the accompanying drawings. Before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, the phraseology and terminology employed herein are for the purpose of description and should not be regarded as limiting.

Therefore the object of the present invention is to provide a fragrant gel polymer system that reduces the formulation and testing requirements of constituent fragrances for potential reactivity with the cross linker or polymer and splitting fragrances into parts.

Another object of the fragrant gel polymer system is to allow for testing the constituent fragrances with any of the polymers and cross linkers.

Another object of the fragrant gel polymer system is to strengthen the color fastness and performance of a gel.

Another object of the fragrant gel polymer system is to produce a gel being more transparent and less cloudy than water based gels using surfactants.

Another object of the fragrant gel polymer system is to reduce syneresis, steric hindrance, gel instability, and product failure.

Another object of the fragrant gel polymer system is to reduce research and development efforts and costs commonly associated with two part split fragrance processes and formulations.

Another object of the present invention is to provide such a gel product that may be easily and efficiently manufactured by allowing longer hold times during manufacturing, reducing waste during manufacturing, and may be and marketed at less cost than existing gels.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWINGS

In referring to the drawings.

The same reference numerals refer to the same parts throughout the various figures.

DESCRIPTION OF THE PREFERRED EMBODIMENT

Figure 1:
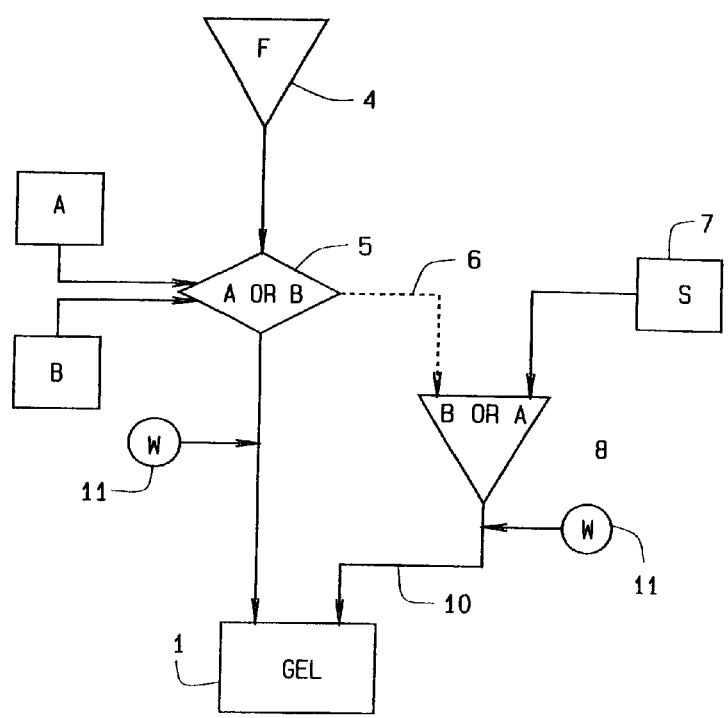
FIG. 1 shows a block diagram of the components and processes of the two part anhydrous embodiment of the fragrant gel polymer system practiced in accordance with the principles of the present invention; and, FIG. 2 provides a block diagram of the processes of the preferred embodiment of the present invention where water and an alcohol are included.

The present art overcomes the prior art limitations by assembling a fragrance formulation from its components then mixing the fragrance with one of two classes of polymer, the fragrance may go in between phases or just in one phase based on our U.S. Pat. No. 7,700,665 for which a solvent can be added as an option, and then mixing the polymer carrying the fragrance with the dissolved polymer resulting in a gel product with minimal syneresis and a more consistent setting time. Though the components of the invention are few in number, the sequence of mixing forms the key to the present invention. Turning to FIG. 1, a block diagram shows the fragrant gel polymer system from initial components to the resulting product.

The present invention 1 begins with the components of a fragrance formulation selected by a fragrance house or manufacturer. A fragrance may have as many components as determined by the designers and chemists of the fragrance house. The present invention then mixes the components to form the fragrance F, generally in a liquid state, as at 4.

The fragrance is then mixed with either a polymer, as at A, or a cross linking agent, as at B, with the mixing step shown as at 5. The polymer derives from butadiene, isoprene or chloroprene. Preferably the polymer, as at A, is maleinized polybutadiene of at least 5000 molecular weight. Alternatively, the polymer includes maleinized polyisoprene of at least 200,000 molecular weight. These polymers are readily available from commercial chemical sources. A preferred polymer is Lithene® by Synthomer®, typically Lithene® N4-9000 10 MA, which is a maleinized polybutadiene of a 9000 molecular weight before maleinization. The other component, a cross-linking agent comes from the amine family of polymers, including polypropoxy diamines, polypropoxy triamines and polyethoxydiamines. A preferred cross linking agent, as at B, is Jeffamine® by Huntsman® Corp., such as the Jeffamine® D-400, which is polyetheramine. In a liquid state, the fragrance is then blended with either a polymer or a cross linking agent. The fragrance carrying polymer then proceeds for further manufacturing as at 9.

Segregated from the fragrance carrying polymer, the polymer or cross linking agent not used in the preceding mixing step, as at 6, is optionally blended as at 8 with a solvent 7. When optionally blended with the solvent, the non-fragrance carrying polymer becomes a homogeneous liquid. Preferably the solvent is benzyl benzoate. Alternatively, the solvent includes di-propylene glycol, isopropyl myristate, alcohol, mineral oil, and the like. Alternatively, the solvent includes substitutes for benzyl benzoate having similar function, particularly esters. Such esters include di-ethyl phthalate, diisoheptyl phthalate a/k/a Jayflex 77® from ExxonMobil of Houston, Tex., triethyl citrate, 2-tert-butylcyclohexyl acetate a/k/a Argumex a/k/a green acetate from Symrise GmbH of Teterboro, N.J. and Holzminden, Germany, diethyl malonate, ethyl benzoate, benzyl butyrate, and methyl benzoate. Di-ethyl phthalate is a plasticizer of low risk to humans with a boiling point of approximately 563° F. Diisoheptyl phthalate a/k/a Jayflex 77® from ExxonMobil of Houston, Tex. is another plasticizer with a flash point of 113° C. Triethyl citrate serves as a plasticizer that also stabilizes foams and it has a boiling point of 235° C. Green acetate, 2-tert-butylcyclohexyl acetate a/k/a Argumex dissolves in alcohol and paraffin oil but not water and it has a boiling point of 221° C. Diethyl malonate also plasticizes perfume formulations while it has a boiling point of 199° C. Ethyl benzoate, a plasticizer, is nearly insoluble in water but blends with others solvents to provide a component for fruit like perfume. Ethyl benzoate has its boiling point of approximately 211° C. Benzyl butyrate does not dissolve in water but does dissolve in alcohol and select oils for use as a plasticizer and while it has a boiling point of approximately 238° C. And, methyl benzoate also does not dissolve in water but blends with organic solvents as a plasticizer to provide a fruit like smell to perfumes. Methyl benzoate has its boiling point of approximately 199° C. The solvents solely modify the viscosity of the non-fragrance carrying polymer and prepare it for mixing with the fragrance carrying polymer, 5, to form a gel.

With the fragrance carrying polymer prepared as at 9 and the non-carrying fragrance polymer ready as at 10, the liquid fragrance carrying polymer is blended with the liquid non-fragrance carrying polymer in a mold to a desired shape, often an air freshener or fragrance sample, thus the present invention forms a gel product 1.

Figure 2:
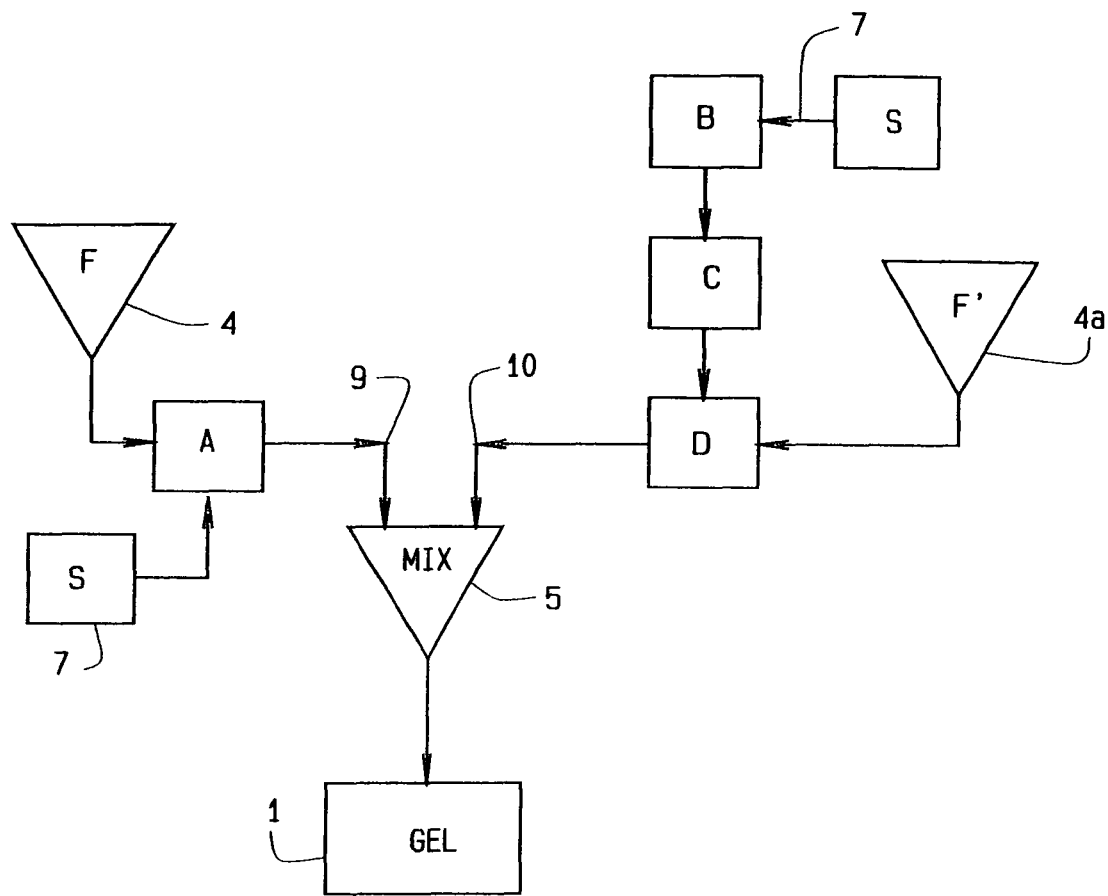

The preferred embodiment of the process for this invention assembles a fragrance formulation from its components then mixing the fragrance in two portions, one with a polymer and the second with a cross linking agent. The cross linking portion then receives water or a wetting agent 11 and an alcohol, preferably ethanol. Then both the polymer portion and the cross linking portion have dyes and solvents added, and then the polymer portion and the cross linking portions are mixed, resulting in a gel product nearly transparent and with reduce steric hindrance from the fragrance materials. Though the components of the invention are few, their mixing sequence again forms the key to the present invention. So, turning to FIG. 2, a block diagram shows the fragrant gel polymer system from initial components to the resulting product.

The present invention 1 begins with the components of a fragrance formulation selected by a fragrance house or manufacturer. As before, a fragrance may have many components provided by third parties, often subject to trade secrets, and at other times unknown. The present invention then separates the fragrance into a major portion F, as at 4, and a minor portion F', as at 4a, generally in a liquid state.

The major portion 4 is then blended with a polymer, as at A, with the later mixing step shown as at 5. The polymer derives from butadiene, isoprene or chloroprene. Preferably the polymer, as at A, is maleinized polybutadiene of at least 5000 molecular weight. Alternatively, the polymer includes maleinized polyisoprene of at least 200,000 molecular weight. These polymers are readily available from commercial chemical sources. A preferred polymer is Lithene® by Synthomer®, typically Lithene® N4-9000 10 MA, which is a maleinized polybutadiene of a 9000 molecular weight before maleinization. In a liquid state, the major portion of the fragrance dissolves into the polymer, preferably Lithene®. The major portion of fragrance is generally miscible with the polymer where the major portion dissolves into the polymer at all proportions.

The polymer with dissolved fragrance then receives various dyes for a select coloration and at least one solvent, S as at 7, to aid in liquefying the polymer and dissolved fragrance. The solvents operate to aid fluid mixing during manufacturing. In the preferred embodiment, the polymer component has about 16% to about 21% by weight of maleinized polybutadiene, about 30% to about 60% by weight of major fragrance portion, an optional solvent, and an optional dye.

Meanwhile as the polymer component is blended, the cross linking agent undergoes separate blending. The cross linking agent comes from the amine family of polymers, including monoamines, polypropoxy diamines, and polyethoxydiamines but not triames. A preferred cross linking agent, as at B, is Jeffamine® by Huntsman® Corp., such as the Jeffamine® D-400, which is polyetheramine. The cross linking agent then has an optional solvent, S as at 7, blended with it also shown at step B.

After blending the cross linking agent, and the optional solvent, the cross linking component achieves a liquid state where the solvent is miscible with the cross linker. Then in the liquid state, the cross linking agent receives aliphatic alcohol and water, as at C, where the aliphatic alcohol is provided by Pride Solvents & Chemicals, Inc., Holtsville, N.Y. The cross linking agent, alcohol, and water are mixed until in a uniform liquid state. The preferred alcohol for the process of the invention is ethanol. Ethanol has two carbon atoms that allow it to dissolve in water at all proportions, that is, ethanol has high miscibility with water. Then the minor portion 4a of fragrance is blended with the cross linking agent component and an accelerator made by Huntsman® but excluding TEA as at step D. The accelerator allows the process of the invention to cure a gel more quickly than it would otherwise.

In the preferred embodiment, the cross linking component has about 1% to about 5% by weight of polyetheramine, about 1% to about 10% by weight of solvent, about 1% to about 8% by weight of aliphatic alcohol, about 1% to about 5% by weight of water, about 0.0001% to about 30% by weight of minor fragrance portion, about 0.05% to about 2% by weight of accelerator, and an optional dye.

With the fragrance carrying polymer component prepared, as at 9, and is the cross linking component ready as at 10, the two components are mixed, as at 5, with the polymer component on the high side and the cross linking component on the low side. The combined solution is then placed in a mold of a desired shape, often an air freshener or fragrance sample, to cure and thus the present invention forms a gel product 1.

From the aforementioned description, a fragrant gel polymer with water system has been described. The system is uniquely capable of combining all of the fragrance components with a polymer and a cross linking agent in liquid form and then mixing the fragrance carrying polymer with the cross linking component, including water, to make a transparent gel product providing a fragrance. The system may be manufactured from many materials, including but not limited to, Lithene®, Jeffamine®, polymers, cross linking agents, water, alcohol, ethanol, solvents, esters, blends and combinations thereof.

We claim:

1. A process for preparing a fragrant gel with reduced steric hindrance comprising the steps of:

blending a mixture A including a major portion of a fragrance oil included in an amount at about 0.0001 to about 30% by weight of the composition, a polymer, and an optional solvent of about 1% to 10% by weight of the composition, said polymer is derived from one of maleinized butadiene having a molecular weight of at least 5,000, maleinized polyisoprene of a molecular weight of at least 200,000, or chloroprene, and wherein said solvent solely modifies the viscosity of said mixture A;

blending a liquid mixture B including a cross linking agent and said solvent, wherein said cross linking agent included in the composition in an amount of about 1% to about 10% by weight, and said cross linking agent derived from one of amine or polyetheramine, said polyetheramine being included in the composition in an amount of 1% to 5% by weight, and wherein said solvent solely modifies the viscosity of the mixture B;

blending a mixture C including said mixture B, water, and a short chain linear alcohol, included in an amount of about 1% to about 8% by weight of the composition;

blending a mixture D including said mixture C and a minor portion of said fragrance oil;

blending mixture A with mixture D;

forming a gel carrying the fragrance following said blending of mixture A with mixture D with a minimum of syneresis and steric hindrance;

the process further comprising blending said mixture D including an accelerator included in an amount of about 0.05% to about 2% by weight of the composition;

wherein said short chain linear alcohol is no longer than pentyl alcohol, and said short chain linear alcohol is one of pentyl alcohol, isopropyl alcohol, ethyl alcohol, and methyl alcohol;

wherein said process reduces premature reaction of said polymer and said cross-linking agent with said fragrance oil;

and wherein said process produces a fragrance carrying gel being generally transparent and that remains together as a whole.

2. The fragrant gel preparing process of claim 1 further comprising:

providing a substrate having at least one recess; and, said forming a gel occurring in a recess of a substrate.

* * * * *